United States Patent
Gschweng et al.

(10) Patent No.: US 12,097,218 B2
(45) Date of Patent: Sep. 24, 2024

(54) METHODS OF MAKING AND USING EMBRYONIC MESENCHYMAL PROGENITOR CELLS

(71) Applicant: Kite Pharma, Inc., Santa Monica, CA (US)

(72) Inventors: Eric Gschweng, Santa Monica, CA (US); Ruben Rodriguez, Santa Monica, CA (US); Yong Ouyang, Santa Monica, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 310 days.

(21) Appl. No.: 15/989,730

(22) Filed: May 25, 2018

(65) Prior Publication Data

US 2018/0369284 A1 Dec. 27, 2018

Related U.S. Application Data

(60) Provisional application No. 62/514,467, filed on Jun. 2, 2017, provisional application No. 62/511,907, filed on May 26, 2017.

(51) Int. Cl.

| A61K 35/17 | (2015.01) |
|---|---|
| C12N 5/00 | (2006.01) |
| C12N 5/0735 | (2010.01) |
| C12N 5/0775 | (2010.01) |
| C12N 5/0783 | (2010.01) |
| C12N 5/074 | (2010.01) |

(52) U.S. Cl.
CPC ............ *A61K 35/17* (2013.01); *C12N 5/0062* (2013.01); *C12N 5/0606* (2013.01); *C12N 5/0636* (2013.01); *C12N 5/0662* (2013.01); *C12N 5/0696* (2013.01); *C12N 2501/125* (2013.01); *C12N 2501/2307* (2013.01); *C12N 2501/26* (2013.01); *C12N 2501/727* (2013.01); *C12N 2506/02* (2013.01); *C12N 2506/13* (2013.01); *C12N 2533/52* (2013.01); *C12N 2533/90* (2013.01)

(58) Field of Classification Search
CPC .... A61K 35/17; C12N 5/0636; C12N 5/0662; C12N 5/0062; C12N 5/0606; C12N 2501/727; C12N 2533/90; C12N 2506/02; C12N 2501/2307; C12N 2533/52; C12N 2501/26; C12N 2506/13; C12N 2501/125; C12N 5/0696
See application file for complete search history.

(56) References Cited

U.S. PATENT DOCUMENTS

| 5,728,388 A | 3/1998 | Terman |
| 5,827,642 A | 10/1998 | Riddell et al. |
| 6,040,177 A | 3/2000 | Riddell et al. |
| 6,797,514 B2 | 9/2004 | Berenson et al. |
| 6,867,041 B2 | 3/2005 | Berenson et al. |
| 6,905,874 B2 | 6/2005 | Berenson et al. |
| 9,855,298 B2 | 1/2018 | Bot et al. |
| 2002/0006409 A1 | 1/2002 | Wood |
| 2010/0136598 A1* | 6/2010 | Strehl ................. C12N 5/0662 435/395 |
| 2013/0287748 A1 | 10/2013 | June et al. |
| 2014/0154228 A1 | 6/2014 | Volk et al. |
| 2015/0191699 A1 | 7/2015 | Wang et al. |
| 2015/0329826 A1* | 11/2015 | Van Den Bos ...... C12N 5/0662 435/325 |
| 2017/0226472 A1* | 8/2017 | Marchal Corrales ........................ C12N 5/0037 |
| 2017/0333403 A1 | 11/2017 | Hosoya et al. |
| 2017/0340586 A1 | 11/2017 | Hosoya et al. |
| 2018/0273891 A1 | 9/2018 | Tanabe et al. |
| 2019/0017029 A1* | 1/2019 | Zhang ................... C12N 5/069 |
| 2021/0085725 A1 | 3/2021 | Wang et al. |
| 2022/0389368 A1 | 12/2022 | Tanabe et al. |

FOREIGN PATENT DOCUMENTS

| WO | 2008081035 A1 | 7/2008 |
| WO | WO2009/006399 A1 | 1/2009 |
| WO | 2012079000 A1 | 6/2012 |
| WO | 2012129514 A1 | 9/2012 |
| WO | WO2017/075389 A1 | 5/2017 |

OTHER PUBLICATIONS

Evseenko et al., including supplemental, PNAS, 107(31): 13742-13747, 2010.*
Stover et al., Methods Mol Biol. 2011 ; 767: 137-146.*
Maldonado et al., Stem Cell Research, 17 (2016) 222-227.*
Takahashi et al., Cell, 131: 12-12, Nov. 30, 2007.*
Chin, 2016, Forming the Hematopoietic Stem Cell Niche from Pluripotent Stem Cells [Doctoral Dissertation, University of California, Los Angeles].*
Ellerstrom et al., Stem Cells, 2007;25:1690-1696.*
"Single Cell Passaging Methods", Gibco® RevitaCell™ Supplement, Life Technologies, pp. 1-4, 2015.*
"Weekend-Free Culture of Human Pluripotent Stem Cells in mTeSR or TESR-E8," Stem Cell Technologies, Document 28071, pp. 1-4, Dec. 2016.*
Jin et al., Tissue Engineering: Part A vol. 18, Nos. 13 and 14, 2012.*
Chen et al. "Non-colony type monolayer culture of human embryonic stem cells."Stem Cell Res. Nov. 2012; 9(3): 237-248. (Year: 2012).*
Hendrich, J.K.; (2008) Alpha-2-delta subunits of voltage-gated calcium channels. Doctoral thesis , University of London. (Year: 2008).*
Yamato et al. "Improving the differentiation potential of pluripotent stem cells by optimizing culture conditions. "Scientific Reports vol. 12, Article No. 14147 (2022) (Year: 2022).*

(Continued)

*Primary Examiner* — Titilayo Moloye

(57) ABSTRACT

The disclosure provides a method of generating non-clustered stem cells. Cluster disruption prior to mesoderm differentiation increases yield and efficiency in hEMP and T cell differentiation. Thus, this method allows the development of improved methods of hEMP and T cell differentiation.

16 Claims, 7 Drawing Sheets

(56) References Cited

OTHER PUBLICATIONS

Ren et al. "Human Bone Marrow Stromal Cell Confluence: Effects on Cell Characteristics and Methods of Assessment. "Cytotherapy. Jul. 2015; 17(7): 897-911. (Year: 2015).*
Balint et al. "Low-density subculture: a technical note on the importance of avoiding cell-to-cell contact during mesenchymal stromal cell expansion."J Tissue Eng Regen Med. Oct. 2015;9(10):1200-3. (Year: 2015).*
Emmanuel Olivier et al., "Differentiation of human embryonic stem cells into bipotent mesenchymal stem cells", Stem Cells 24: 1914-1922 (2006).
Y.S. Chen et al., "Small molecule mesengenic induction of human induced pluripotent stem cells to generate mesenchymal stem/stromal cells." Stem Cells Translational Medicine, pp. 83-95, vol. 1 No. 2 (2012).
Michelle J. Smith et al., "In vitro T-cell generation from adult, embryonic, and induced pluripotent stem cells: many roads to one destination", Stem Cells, vol. 33 No. 11, pp. 3174-3180 (2015).
Cheung et al., "Epitope-specific antibody response to the surface antigen of duck hepatitis B virus in infected ducks", Virology, 176(2) 1990.
Dayhoff et al., "Atlas of Protein Sequence and Structure: A Model of Evolutionary Change in Proteins", 5: 1978.
Devereux et al., "A comprehensive set of sequence analysis programs for the VAX", Nucl. Acid Res., 12: 1984.
Henikoff et al., "Amino acid substitution matrices from protein blocks", Proc. Natl. Acad. Sci. U.S.A., 89(22): 1992.
Kirkland et al., "Analysis of the fine specificity and cross-reactivity of monoclonal anti-lipid A antibodies", J. Immunol. 5 137(11): 1986.
Moldenhauer et al., "Identity of HML-1 antigen on intestinal intraepithelial T cells and of B-ly7 antigen on hairy cell 6 leukaemia", Scand. J. Immunol., 32(2): 1990.
Morel et al., "Monoclonal antibodies to bovine serum albumin: affinity and specificity determinations", Molec. Immunol., 7 25(1): 1988.
Seet et al., "Generation of mature T cells from human hematopoietic stem/progenitor cells in artificial thymic 8 organoids", Nature methods, 14(5): 2017.
Stahli et al., "Distinction of epitopes by monoclonal antibodies", Methods in Enzymology, 92: 1983.
Raynaud, et al., "Human Embryonic Stem Cell Derived Mesenchymal Progenitors Express Cardiac Markers but Do Not Form Contractile Cardiomyocytes", PLOS One, vol. 8, Issue 1, Jan. 2013, pp. 1-13.
English Translation of Office Action mailed Jan. 5, 2021 for Japanese Patent Application No. 2019-565288, 14 pages.
English Translation of Notice of Preliminary Rejection for Korean Patent Application No. 10-2019-7037737, 4 pages.
Office Action, issued in CA Application No. 3064018, dated Feb. 25, 2021.
Examination Report issued in AU Application No. 2018272017 dated Mar. 29, 2021.
Office Action dated Jun. 22, 2021 for Japanese Appl. No. 2019-565288.
Office Action dated Jul. 24, 2021 for Korean Appl. No. 10-2019-7037737.
Office Action dated Aug. 31, 2021 for Saudi Arabian Appl. No. 519410835.
Office Action dated Oct. 20, 2021 for Korean Appl. No. 10-2021-7029826.
Office Action dated Oct. 22, 2021 for Korean Appl. No. 10-2019-7037737.
Office Action dated Dec. 17, 2021 for New Zealand Appl. No. 759234.
Intl. Search Report—Written Opinion dated Sep. 3, 2018 for PCT/US2018/034567.
Examination Report dated May 11, 2022 for New Zealand Appl. No. 759234.
Examination Report dated Mar. 7, 2022 for Saudi Arabian Appl. No. 2006/15251.
Office Action dated Jun. 21, 2022 for Argentinian Appl. No. 20180101387.
Office Action dated Dec. 10, 2021 for Canadian Appl. No. 3,064,018.
Office Action dated Jul. 23, 2022 for Korean Appl. No. 10-2022-7009776.
Office Action dated Aug. 2, 2022 for Taiwanese Appl. No. 107118001.
Chen, K.G. et al. (2014) "Human Pluripotent Stem Cell Culture: Considerations for Maintenance, Expansion, and Therapeutics" Cell Stem Cell 14(1):13-26.
Rowland, T.J. et al. (2010) "Roles of Integrins in Human Induced Pluripotent Stem Cell Growth on Matrigel and Vitronectin" Stem Cells and Development 19(8):1231-1240.
Office Action dated Oct. 31, 2022 for Canadian Appl. No. 3,064,018.
Watanabe, K. et al. (2007) "A ROCK inhibitor permits survival of dissociated human embryonic stem cells" Nat. Biotechnology 25(6):686-686.
Choo, A. et al. (2011) "Chapter 12: Derivation of Mesenchymal Stem Cells from Human Embryonic Stem Cells" Embryonic Stem Cell Therapy for Osteo-Degenerative Diseases, Methods in Molecular Biology 690:175-182.
Office Action dated Dec. 21, 2022 for Japanese Appl. No. 2022-006815.
Office Action dated Nov. 25, 2022 for Chinese Appl. No. 201880034504.1.
Office Action dated Jan. 2, 2023 for Israeli Appl. No. 270770.
Office Action dated Jan. 27, 2023 for Korean Appl. No. 10-2022-7009776.
Office Action dated Mar. 1, 2023 for European Appl. No. 18730936.4.
Office Action dated May 23, 2023 for Japanese Appl. No. 2022-006815.
Office Action dated Jun. 27, 2023 for Korean Appl. No. 10-2022-7009776.
Office Action dated Apr. 25, 2023 for Taiwanese Appl. No. 107118001.
Office Action dated Jul. 26, 2023 for Chinese Appl. No. 201880034504.1.
Office Action dated Sep. 26, 2023 for Japanese Appl. No. 2022-006815.
Office Action dated Oct. 12, 2023 for Emirati Appl. No. P6001660/2019.
Office Action dated Dec. 22, 2023 for Canadian Appl. No. 3064018.
Office Action dated Jan. 4, 2024 for Chinese Appl. No. 201880034504.1.

* cited by examiner

METHODS OF MAKING AND USING EMBRYONIC MESENCHYMAL PROGENITOR CELLS

CROSS REFERENCE TO RELATED APPLICATIONS

This application claims priority to U.S. Provisional Application No. 62/511,907 filed May 26, 2017 and U.S. Provisional Application No. 62/514,467, filed Jun. 2, 2017, both of which are incorporated by reference herein, in their entirety.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's immune system to specifically target and kill cancer cells. However, cancer cells employ various mechanisms to prevent immune cells, such as T and B lymphocytes, from successfully targeting cancer cells.

Current T cell therapies rely on enriched or modified human T cells to target and kill cancer cells in a patient. Patient or normal donor derived T cells are finite by nature as they lack self-renewal. The derivation of T cells from a stem cell source would provide a potentially unlimited source of cells for therapeutic use. A need exists for efficient in vitro methods for differentiation of pluripotent stem cells to embryonic mesodermal progenitors and mature T cells.

SUMMARY

The present invention addresses this need by, among other things, providing improved methods for generating human embryonic mesenchymal progenitor (hEMP) cells, their derivatives, and the use of the same for efficient generation of T cells.

In one aspect, the present disclosure provides a method of generating human embryonic mesenchymal progenitor (hEMP) cells, the method comprising the steps of contacting non-clustered stem cells with a substrate at a defined single cell density; cultivating the stem cells under culture conditions that facilitate cell growth to a desired confluence; and modifying the culture conditions to induce differentiation of the stem cells into hEMP cells for a desired incubation time; thereby generating hEMP cells.

In some embodiments, the non-clustered stem cells are human embryonic stem (ES) cells or induced pluripotent stem (iPS) cells. In some embodiments, the ES or iPS cells are human in origin.

In some embodiments, the ES or iPS cells are H1 cells, H9 cells, HES3 cells, HSF1 cells, HSF6 cells, ESI-017 cells, CS02iCTR-NTn1 cells, CS03iCTR-NTn1 cells, CS80iCTR-Tn3 cells, CS179iCTR-NTn1 cells, CS201iCTR-NTn4 cells, CS202iCTR-NTn2 cells, or CS206iCTR-Tn5 cells.

In some embodiments, the defined single cell density is between about $1.5 \times 10^5$ and about $8 \times 10^5$ cells/cm$^2$. In certain embodiments, the defined single cell density is about $1.89 \times 10^5$ cells/cm$^2$, about $3.2 \times 10^5$ cells/cm$^2$, about $3.4 \times 10^5$ cells/cm$^2$, about $3.6 \times 10^5$ cells/cm$^2$, about $3.79 \times 10^5$ cells/cm$^2$, about $7.2 \times 10^5$ cells/cm$^2$, or about $7.58 \times 10^5$ cells/cm$^2$.

In some embodiments, the substrate is coated with Matrigel® or recombinant human vitronectin, but not mouse embryonic fibroblasts (MEFs). In some embodiments, the substrate is a welled plate, a cell culture dish, a membrane, a bag, a culture flask, an inverse opal, a polymer lattice, a static cell suspension, an agitated cell suspension, or a plasma treated polymer. In some embodiments, the substrate comprises a membrane.

In some embodiments, the culture conditions that facilitate cell growth comprise cultivating the stem cells in mTeSR1 media. In some embodiments, the mTeSR1 media further comprises a ROCK inhibitor. In certain embodiments, the mTeSR1 media further comprises the ROCK inhibitor Y27632.

In some embodiments, cells are grown to a desired confluence between about 20% and about 80%. In some embodiments, the confluence is about 20%, about 30%, about 40%, about 50%, about 60%, about 70% or about 80%.

In some embodiments, the step of modifying the culture conditions comprises culturing cells in X-VIVO™ 15 culture media.

In some embodiments, the incubation time is between about 2 and about 4 days. In some embodiments, the incubation time is about 2.0, about 2.5, about 3.0, about 3.5 or about 4.0 days. In certain embodiments, the incubation time is about 3.5 days.

In some embodiments, the method further comprises the step of differentiating the hEMP cells into T cells.

In some embodiments, the method further comprises a step of disrupting clusters of stem cells to generate the non-clustered stem cells. In some embodiments, the clusters of stem cells are disrupted by mechanical or chemical disruption. In some embodiments, the chemical disruption comprises incubation with Trypsin-like enzyme (TrypLE). In certain embodiments, the Trypsin-like enzyme is Trypsin, TrypLE Express, TrypLE Select, collagenase, dispase, or Trypsin-EDTA.

In some embodiments, a human embryonic mesenchymal progenitor (hEMP) cell is generated according to a method described herein.

In one aspect, the present disclosure provides a composition comprising a population of human embryonic mesenchymal progenitor (hEMP) cells generated according to a method described herein.

In one aspect, the present disclosure provides a method of generating T cells, the method comprising the steps of: contacting non-clustered stem cells with a substrate at a defined single cell density, wherein the stem cells do not comprise mouse embryonic fibroblasts (MEFs); cultivating the stem cells under culture conditions that promote cell growth to a desired confluence; and modifying the culture conditions to induce differentiation of the stem cells into T cells for a desired incubation time; whereby generating T cells from stem cells.

In some embodiments, the stem cells are human embryonic stem (ES) cells or induced pluripotent stem (iPS) cells. In some embodiments, the ES or iPS cells are human in origin.

In some embodiments, the ES or iPS cells are H1 cells, H9 cells, HES3 cells, HSF1 cells, HSF6 cells, ESI-017 cells, CS02iCTR-NTn1 cells, CS03iCTR-NTn1 cells, CS80iCTR-Tn3 cells, CS179iCTR-NTn1 cells, CS201iCTR-NTn4 cells, CS202iCTR-NTn2 cells, or CS206iCTR-Tn5 cells.

In some embodiments, the defined single cell density is between about $1.5 \times 10^5$ and about $8 \times 10^5$ cells/cm$^2$. In certain embodiments, the defined single cell density is about $1.89 \times$ $10^5$ cells/cm$^2$, about 3.2×10$^5$ cells/cm$^2$, about 3.4×10$^5$ cells/cm$^2$, about 3.6×10$^5$ cells/cm$^2$, about 3.79×10$^5$ cells/cm$^2$, about 7.2×10$^5$ cells/cm$^2$, or about 7.58×10$^5$ cells/cm$^2$.

In some embodiments, the substrate is coated with Matrigel® or recombinant human vitronectin, but not mouse embryonic fibroblasts (MEFs). In some embodiments, the substrate is a welled plate, a cell culture dish, a membrane, a bag, a culture flask, an inverse opal, a polymer lattice, a static cell suspension, an agitated cell suspension, or a plasma treated polymer. In some embodiments, the substrate comprises a membrane.

In some embodiments, the culture conditions that facilitate cell growth comprise cultivating the stem cells in mTeSR1 media. In some embodiments, the mTeSR1 media further comprises a ROCK inhibitor. In certain embodiments, the mTeSR1 media further comprises the ROCK inhibitor Y27632.

In some embodiments, cells are grown to a desired confluence between about 20% and about 80%. In some embodiments, the confluence is about 20%, about 30%, about 40%, about 50%, about 60%, about 70% or about 80%.

In some embodiments, the step of modifying the culture conditions comprises culturing cells in X-VIVO™15 culture media.

In some embodiments, the incubation time is between about 2 and about 4 days. In some embodiments, the incubation time is about 2.0, about 2.5, about 3.0, about 3.5 or about 4.0 days. In certain embodiments, the incubation time is about 3.5 days.

In one aspect, the present disclosure provides a T cell generated according to a method described herein.

In one aspect, the present disclosure provides a composition comprising a population of T cells generated according to a method described herein.

Any aspect or embodiment described herein may be combined with any other aspect or embodiment as disclosed herein. While the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, dictionaries, documents, manuscripts and scientific literature cited herein are hereby incorporated by reference.

Other features and advantages of the disclosure will be apparent from the Drawings and the following Detailed Description, including the Examples, and the claims.

BRIEF DESCRIPTION OF THE DRAWINGS

The above and further features will be more clearly appreciated from the following detailed description when taken in conjunction with the accompanying drawings. The drawings however, are for illustration purposes only, not for limitation.

DEFINITIONS

Figure 1:
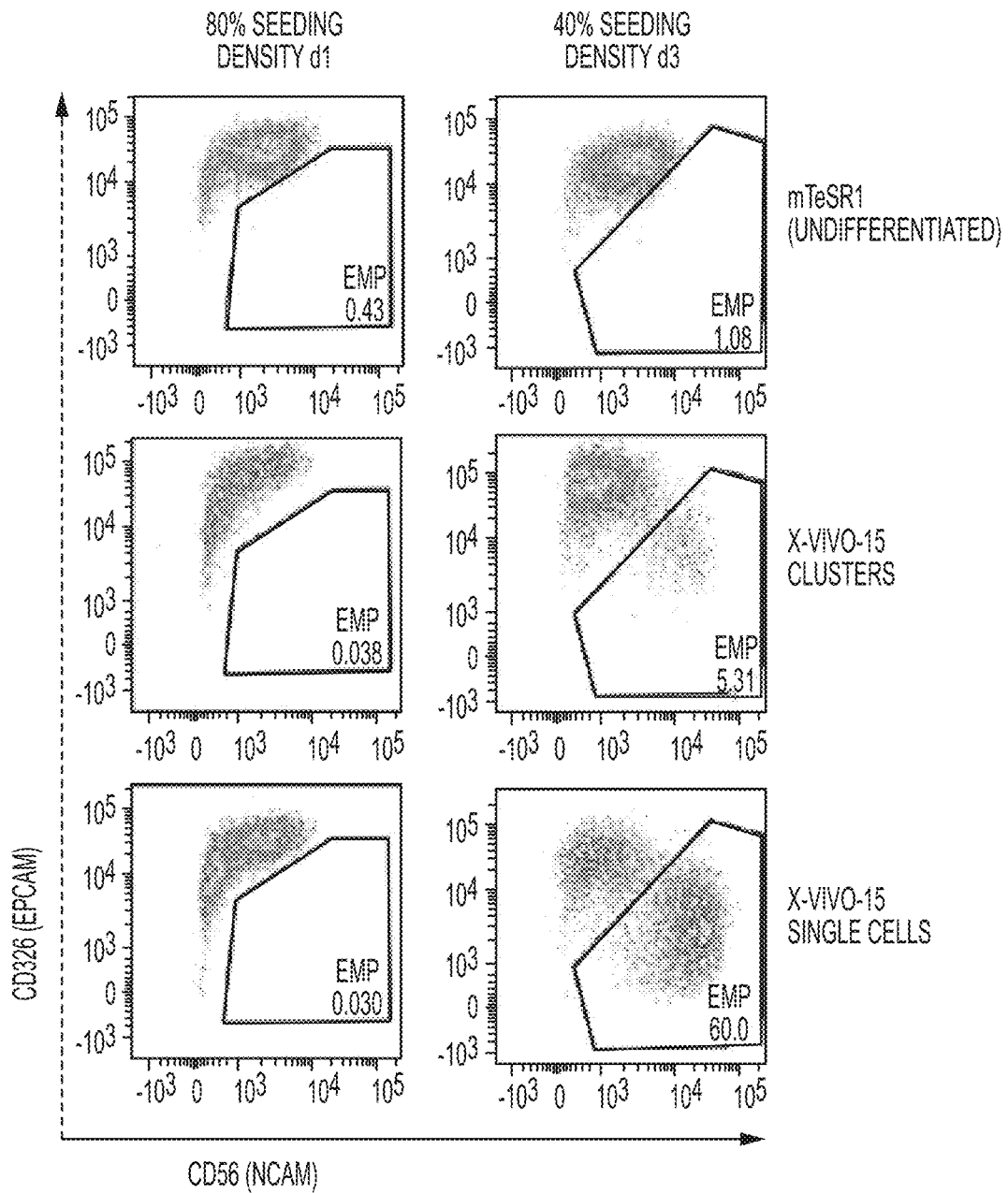
FIG. 1 shows exemplary flow cytometry data illustrating the change in surface expressed CD326 and CD56.

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and."

The term "and/or" where used herein is to be taken as specific disclosure of each of the two specified features or components with or without the other. Thus, the term "and/or" as used in a phrase such as "A and/or B" herein is intended to include A and B, A or B, A (alone), and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intra-arterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal, or mucosal route of administration, for example, intranasally, vaginally, rectally, sublingually or topically. Administering can also be performed, for example, once, a plurality of times, and/or over one or more extended periods.

As used herein, an antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15), solid phase direct biotin-avidin EIA (Cheung, et al., 1990, Virology 176:546-552), and direct labeled RIA (Moldenhauer et al., 1990, Scand. J. Immunol. 32:77-82).

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, could serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens.

The term "allogeneic" refers to any material derived from one individual, which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may metastasize to distant parts of the body through the lymphatic system or bloodstream. A "cancer" or "cancer tissue" can include a tumor. Examples of cancers that can be treated by the methods of the present disclosure include, but are not limited to, cancers of the immune system including lymphoma, leukemia, myeloma, and other leukocyte malignancies. In some embodiments, the methods of the present disclosure can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory TSCM cells, like naive cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). They make antibodies and antigens, perform the role of antigen-presenting cells (APCs), and turn into memory B-cells after activation by antigen interaction. In mammals, immature B-cells are formed in the bone marrow.

The term "genetically engineered", "engineered", or "modified" refers to a method of modifying a cell, including, but not limited to, creating a deficiency in a gene by deleting a coding or non-coding region or a portion thereof or by antisense technology, or increasing expression of a protein introducing a coding region or a portion thereof. In some embodiments, the cell that is modified is a stem cell (e.g., hematopoietic stem cell (HSC), embryonic stem cell (ES), induced pluripotent stem (iPS) cell), lymphocyte (e.g., a T cell), which can be obtained either from a patient or a donor.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing, or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population; induced pluripotent stem cells (iPS), embryonic stem cells (ES), or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. A "patient" as used herein includes any human who is afflicted with a cancer (e.g., a lymphoma or a leukemia). The terms "subject" and "patient" are used interchangeably herein.

As used herein, the term "in vitro cell" refers to any cell, which is cultured ex vivo. In particular, an in vitro cell can include a T cell.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, which specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand" as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD33, CD45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD1 1a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein, and indicate any change that is less than the original. "Reducing" and "decreasing" are relative terms, requiring a comparison between pre- and post-measurements "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity, or recurrence of a symptom, complication or condition, or biochemical indicia associated with a disease. In one embodiment, "treatment" or "treating" includes a partial remission. In another embodiment, "treatment" or "treating" includes a complete remission.

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm.) In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

As used herein, the term "disruption" or "disrupt" refers to the mechanical, chemical, and/or enzymatic dissociation of clustered cells. As used herein, disrupted cells remain intact but loose cell-cell adhesion contacts as well as membrane adhesion properties.

As used herein, the term "cultivation" or grammatical equivalents refers to a process of maintaining cells under conditions favoring growth, survival, or differentiation. The terms "cultivation" and "cell culture" or any synonyms are used inter-changeably in this application.

As used herein, the term "cell density" or "single cell density" refers to the amount of cells in a volume or surface area. In some embodiments, cell density is expressed in cells/well of a six-well plate. According to the present disclosure, a standard six well plate has a surface area of approximately 9.5 cm$^2$. In some embodiments, cell density is expressed as cells/cm$^2$.

As used herein, the term "culture vessel" refers to any container that can provide an aseptic environment for culturing cells. Exemplary culture vessels include, but are not limited to, glass, plastic, or metal containers.

Various aspects of the disclosure are described in further detail in the following subsections.

DETAILED DESCRIPTION

According to the present disclosure, HSC or other stem cells (embryonic stem (ES) or induced pluripotent stem (iPS)) may be used to generate a large, perhaps infinite, number of engineered T cells with desired lineage. The present disclosure provides, among other things, highly efficient methods for the differentiation of human embryonic stem (ES) or induced pluripotent stem (iPS) cells to embryonic mesodermal progenitors (hEMP) and/or T cells, and compositions comprising the same.

Without wishing to be bound of any particular theory, it is contemplated that the generation of T cells from ES or iPS cells is more efficient if preceded by an induction step called a "mesoderm push" or hEMP induction. Briefly, ES or iPS cells are cultured, passaged, and grown until a desired confluence. Subsequently, culture conditions are changed to hEMP induction medium. In some embodiments, the method of culturing ES or iPS cells is feeder free (i.e. no MEFs) on either Matrigel® or recombinant human vitronectin. Surprisingly, the present inventors have discovered that hEMP can be more efficiently generated if non-clustered cell cultures are used for "mesoderm push" or hEMP induction. For example, non-clustered stem cells may be seeded on a substrate at a defined single cell density, and induced. The result is an efficient and reproducible mesoderm push. High yield of hEMP cells from the mesoderm push allows for efficient, rapid, and robust T cell differentiation in downstream applications.

Pluripotent Stem Cells

Various pluripotent stems cells may be used to practice the present disclosure. For example, hematopoietic stem cells (HSC) in the bone marrow (also cord blood or peripheral blood) give rise, in addition to all other mature blood cells, to committed thymic progenitors. These thymic progenitors traffic to the thymus where they begin their development to mature T cells. The signaling of Notch receptors via their ligands Delta and Jagged, particularly Notch1 and Delta like 4 in the thymus, drives a transcriptional cascade (i.e. Tcf7, Gata3, Bcl11b, etc.) that results in the rearrangement of TCR loci by the recombinase activating genes RAG1 and RAG2. First, a productive TCRb rearrangement (i.e. resulting in a TCR protein) will generate a protein that pairs with pTa and traffics to the surface. This surface trafficking conveys a signal back to the cell that allows it to proceed to further development. The surface pTa-TCRb need not interact with MHC as occurs in a mature TCR—the survival signal may be peptide:MHC independent. The cell then proceeds to rearrange TCRa, is scrutinized for successful alpha/beta pairing and weak recognition of self-peptide:MHC (i.e. positive and negative selection or central tolerance) before becoming a mature naïve T cell and circulating to the periphery.

In some embodiments, embryonic stem (ES) or induced pluripotent stem (iPS) cells may be used.

Stem cells may be acquired from any source known in the art. For example, induced pluripotent stem cells (iPS) or embryonic stem cells (ES) can be obtained from commercial sources. Suitable HSCs, ES cells, iPS cells and other stems cells may also be cultivated immortal cell lines or isolated directly from a patient. Various methods for isolating, developing, and/or cultivating stem cells are known in the art and can be used to practice the present disclosure.

Generating Non-Clustered Stem Cells

As described herein, cultivating non-clustered single cell stem cells in suspension prior to mesoderm induction results in increased efficiency of stem cell differentiation. Various methods may be used to generate non-clustered stem cell cultures. For example, ES or iPS cells can be first cultured as clusters on mouse embryonic fibroblasts (MEFs), Matrigel®, or vitronectin and passaged as clusters onto Matrigel® or vitronectin coated plates. In some embodiments, in order to generate single cells in suspension, clusters are chemically disrupted by digestion with Trypsin, Trypsin-like enzyme, or other cell-cell adhesion disruptors known in the art. In some embodiments, clusters are mechanically disrupted by homogenization (e.g., resuspension, mechanical stirring, media wash, buffer wash, cell dissociator (e.g. Miltenyi GentleMACS), or vortex) in order to generate single cells in suspension.

In some embodiments, culture conditions are adapted to promote single cell growth so that the stem cells do not form clusters. For example, stem cells may be grown in suspension.

Substrates

According to the present disclosure, non-clustered stem cells are seeded on a substrate at a defined single cell density for growth. As used herein, the term "substrate" refers to any solid or semi-solid surface or support. For example, a suitable substrate may be a layer, a microbead, a welled plate, a cell culture dish, a membrane, a bag, a culture flask, a vessel, an inverse opal, a polymer lattice, a gel, or a polymer.

In some embodiments, a suitable substrate can be treated with a desired coating. For example, a suitable substrate may be coated with Matrigel® or vitronectin. In some embodiments, a suitable substrate is coated with collagen (e.g. collagen I, II, II, or IV), gelatin, fibronectin, laminin, vitronectin, fibrinogen, BD Matrigel®, basement membrane matrix, dermatan sulfate proteoglycan, Poly-D-Lysine, and/or combinations thereof.

According to the present disclosure, non-clustered cells are seeded on a substrate at a defined single cell density. Single cell density suitable for the present disclosure may range from about $1.0\text{-}50\times10^6$ cells/well in a standard 6-well plate (e.g., about $1.0\text{-}40\times10^6$ cells/well, about $1.0\text{-}30\times10^6$ cells/well, about $1.0\text{-}20\times10^6$ cells/well, about $1.0\text{-}10\times10^6$ cells/well, $1.0\text{-}8\times10^6$ cells/well, about $1.0\text{-}5\times10^6$ cells/well, about $1.0\text{-}4.5\times10^6$ cells/well, about $1.0\text{-}4\times10^6$ cells/well, about $1.0\text{-}3.6\times10^6$ cells/well, about $1.0\text{-}3\times10^6$ cells/well, about $1.0\text{-}2.5\times10^6$ cells/well, about $1.0\text{-}2.0\times10^6$ cells/well, about $1.0\text{-}1.5\times10^6$ cells/well, about $1.5\text{-}10\times10^6$ cells/well, about $1.5\text{-}8\times10^6$ cells/well, about $1.5\text{-}4\times10^6$ cells/well, about $1.5\text{-}3.5\times10^6$ cells/well, about $1.5\text{-}3.0\times10^6$ cells/well, about $1.5\text{-}2.5\times10^6$ cells/well, about $1.5\text{-}2.0\times10^6$ cells/well).

In some embodiments, the cells are passaged at a defined single cell density (e.g., about $1.8\times10^6$ cells/well, about $3.6\times10^6$ cells/well, about $7.2\times10^6$ cells/well).

In some embodiments, the cells are passaged at a cell density ranging from about $1.5\times10^5$ and about $8\times10^5$ cells/cm$^2$ (e.g., $1.89\times10^5$ cells/cm$^2$, about $3.2\times10^5$ cells/cm$^2$, about $3.4\times10^5$ cells/cm$^2$, about $3.6\times10^5$ cells/cm$^2$, about $3.79\times10^5$ cells/cm$^2$, about $7.2\times10^5$ cells/cm$^2$, or about $7.58\times10^5$ cells/cm$^2$).

In some embodiments, defined single cell density at seeding is expressed as a percent confluence. According to the present disclosure, are seeded at defined cell density such that the surface confluence ranges from 1% to 100% (e.g., about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 99%). In some embodiments, cells are passaged at a high percent confluence (e.g., about 70-100%, about 80%). In some embodiments, cells are passaged at a medium percent confluence (e.g., about 30-70%, about 40%). In some embodiments, cells are passaged at a low percent confluence (e.g., about 1-30%, about 20%).

In some embodiments, cells are seeded in growth medium. In other embodiments, cells are seeded in induction medium. In some embodiments, cells are seeded in induction medium, grown to a desired confluence according to the present disclosure and replated in induction medium.

Cell Culture Conditions

According to the present disclosure, ES or iPS cells may be adapted to grow as single cells in suspension culture. In some embodiments, ES or iPS cells are maintained in suspension. ES or iPS cells suspended in nutrient medium may be maintained with a circulation device which ensures that the isolated cells remain in suspension in the nutrient medium.

Culture Media

Various cell culture medium and conditions may be used according to the present disclosure. For example, cells may be produced in serum-containing or serum-free cell culture medium. In some embodiments, the medium is serum-free medium. In some embodiments, the culture medium is an animal free medium, i.e., a medium that lacks animal-derived components. In some embodiments, the medium is a chemically defined medium. As used herein, the term "chemically-defined nutrient medium" refers to a medium of which substantially all of the chemical components are known. In some embodiments, a chemically defined nutrient medium is free of animal-derived components such as serum, serum derived proteins (e.g., albumin or fetuin), and other components. In some cases, a chemically-defined medium comprises one or more proteins (e.g., protein growth factors or cytokines.) In some cases, a chemically-defined nutrient medium comprises one or more protein hydrolysates. In other cases, a chemically-defined nutrient medium is a protein-free media, i.e., a serum-free media that contains no proteins, hydrolysates, or components of unknown composition.

In some embodiments, a chemically defined medium may be supplemented by one or more animal derived components. Such animal derived components include, but are not limited to, fetal calf serum, horse serum, goat serum, donkey serum, human serum, and serum derived proteins such as albumins (e.g., bovine serum albumin or human serum albumin).

In certain embodiments, certain preferable attributes or growth under particular conditions may be chosen for culturing cells. It will be appreciated by one skilled in the art, such attributes may be ascertained based on known characteristic and/or traits of an established line (i.e. a characterized and/or commercially available cell line) or though empirical evaluation. In some embodiments, a cell line may be selected for its ability to grow on a feeder layer of cells. In some embodiments, a cell line may be selected for its ability to grow as an adherent monolayer of cells. In some embodiments, the methods involve comprising culturing stem cells and/or progenitor cells in a cell culture comprising culture medium.

According to the present disclosure, generating human embryonic mesenchymal progenitor (hEMP) cells comprises a growth phase and differentiation phase. In some embodiments, the culture medium during the growth phase is substantially different from the culture medium during the differentiation phase. In certain embodiments, mTESR1 medium is used for the growth phase and X-VIVO™ 15 medium is used for the differentiation phase.

Various culture media can be utilized. Illustrative, but non-limiting culture media include, but are not limited to MEM (Minimal Essential Medium), DMEM (Dulbecco's Modified Eagle's Medium), BME (Basal Medium Eagle), RPMI 1640, DMEM/F-12 (Dulbecco's Modified Eagle's Medium: Nutrient Mixture F-12), DMEM/F-10 (Dulbecco's Modified Eagle's Medium: Nutrient Mixture F-10), a-MEM (a-Minimal essential Medium), G-MEM (Glasgow's Minimal Essential Medium), FMDM (Isocove's Modified Dulbecco's Medium), essential 8 (E8) medium, KnockOut DMEM, AIM V, mTeSR™ 1, X-VIVO™ 15, StemSpan, CellGro Dendritic Cell Medium.

In some embodiments, a feeder-free cell culture medium for human embryonic stem cells (ES cells) and induced pluripotent stem cells (iPS cells) is used. In some embodiments, the present disclosure is used generate non-clustered ES or iPS cell. In some embodiments, a serum-free medium suitable for the disclosure lacks animal-derived components. In some embodiments, a serum-free medium suitable for the disclosure is a chemically-defined medium. For example, mTeSR™1 media may be used for cell growth. MTeSR™1 is a highly specialized, serum-free, and complete cell culture medium.

In certain embodiments, the culture media is supplemented with an inhibitor of the Rho-associated protein kinase (ROCK) pathway (e.g., Y27632). The ROCK inhibitor may be used to aid in reprogramming, maintenance, self-renewal, and/or differentiation.

Desired Confluence at Induction

According to the present disclosure, non-clustered cells are resuspended in or transferred to induction medium and plated on a substrate at a defined single cell density. Single cell density suitable for the present disclosure may range from about $1.0$-$50 \times 10^6$ cells/well in a standard 6-well plate (e.g., about $1.0$-$40 \times 10^6$ cells/well, about $1.0$-$30 \times 10^6$ cells/well, about $1.0$-$20 \times 10^6$ cells/well, about $1.0$-$10 \times 10^6$ cells/well, $1.0$-$8 \times 10^6$ cells/well, about $1.0$-$5 \times 10^6$ cells/well, about $1.0$-$4.5 \times 10^6$ cells/well, about $1.0$-$4 \times 10^6$ cells/well, about $1.0$-$3.6 \times 10^6$ cells/well, about $1.0$-$3 \times 10^6$ cells/well, about $1.0$-$2.5 \times 10^6$ cells/well, about $1.0$-$2.0 \times 10^6$ cells/well, about $1.0$-$1.5 \times 10^6$ cells/well, about $1.5$-$10 \times 10^6$ cells/well, about $1.5$-$8 \times 10^6$ cells/well, about $1.5$-$4 \times 10^6$ cells/well, about $1.5$-$3.5 \times 10^6$ cells/well, about $1.5$-$3.0 \times 10^6$ cells/well, about $1.5$-$2.5 \times 10^6$ cells/well, about $1.5$-$2.0 \times 10^6$ cells/well).

In some embodiments, non-clustered cells are resuspended in or transferred to induction medium and plated on a substrate at a defined single cell density (e.g., $1.8 \times 10^6$ cells/well, about $3.6 \times 10^6$ cells/well, about $7.2 \times 10^6$ cells/well).

In some embodiments, non-clustered cells are resuspended in or transferred to induction medium and plated on a substrate at a defined single cell density ranging between about $1.5 \times 10^5$ and about $8 \times 10^5$ cells/cm$^2$ (e.g., $1.89 \times 10^5$ cells/cm$^2$, about $3.2 \times 10^5$ cells/cm$^2$, about $3.4 \times 10^5$ cells/cm$^2$, about $3.6 \times 10^5$ cells/cm$^2$, about $3.79 \times 10^5$ cells/cm$^2$, about $7.2 \times 10^5$ cells/cm$^2$, or about $7.58 \times 10^5$ cells/cm$^2$).

In some embodiments, defined single cell density at induction is expressed as a percent confluence. According to the present disclosure, non-clustered cells are resuspended in or transferred to induction medium and plated on a substrate at a defined cell density such that the surface confluence ranges from 1% to 100% (e.g., about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 99%). In some embodiments, cells are induced at a high percent confluence (e.g., about 70-100%, about 80%). In some embodiments, cells are induced at a medium percent confluence (e.g., about 30-70%, about 40%). In some embodiments, cells are induced at a low percent confluence (e.g., about 1-30%, about 20%).

Growth and Differentiation Phase

In some embodiments, cells are cultured at a temperature ranging from about 30-37° C. (e.g., about 31-37° C., about 32-37° C., about 33-37° C., about 34-37° C., about 35-37° C., about 36-37° C.). In some embodiments, the cells are cultured at a temperature of approximately 30° C., 31° C., 32° C., 33° C., 34° C., 35° C., 36° C., or 37° C. Any of the temperatures described herein may be used for growth and/or differentiation phase. In some embodiments, cells are cultured at different temperatures during the growth phase and the differentiation phase. In some embodiments, cells are cultured at substantially the same temperatures during the growth phase and the differentiation phase. Any of the medium pH described herein may be used for growth and/or differentiation phase. In some embodiments, the medium pH for the growth phase and the differentiation phase is different. In some embodiments, the medium pH for the growth phase and the differentiation phase is substantially the same.

In some embodiments, ES or iPS cells are grown and maintained in a growth phase. In some embodiments, ES or iPS cells are seeded and grown to a desired confluency (e.g., about 20%, about 30%, about 40%, about 50%, about 60%, about 70%, about 80%, or about 90% confluence) before the differentiation phase. In other embodiments, ES or iPS cells are not seeded prior to the differentiation phase. In certain embodiments, ES or iPS cells are resuspended in differentiation medium and plated at a desired confluency (e.g., about 20%, about 30%, about 40%, about 50%, about 60%, about 70%, about 80%, or about 90% confluence). In some embodiments, ES or iPS cells are cultivated on Matrigel® or vitronectin during the growth phase. In some embodiments, ES or iPS cells are cultivated on mouse embryonic fibroblasts (MEFs) during the growth phase.

In some embodiments, the incubation time for the growth phase is about 1-6 days (e.g., about 1-5 days, about 1-4 days, about 1-3 days, about 1-2 days, about 1 day, about 2 days, about 2.5 days, about 3 days, about 3.5 days, about 4 days). In some embodiments, the incubation time for the growth phase occurs in two steps, wherein the culture is seeded. In some embodiments, each step of the growth phase is about 1-6 days (e.g., about 1-5 days, about 1-4 days, about 1-3 days, about 1-2 days, about 1 day, about 2 days, about 2.5 days, about 3 days, about 3.5 days, about 4 days). In some embodiments, the differentiation phase lasts for about 2, 3, 4, 5, 6, or 7 days.

In some embodiments, the incubation time for the differentiation phase is about 1-6 days (e.g., about 1-5 days, about 1-4 days, about 1-3 days, about 1-2 days, about 1 day, about 2 days, about 2.5 days, about 3 days, about 3.5 days, about 4 days). In some embodiments, the incubation time for the differentiation phase occurs in two steps, wherein the culture is replated. In some embodiments, each step of the differentiation phase is about 1-6 days (e.g., about 1-5 days, about 1-4 days, about 1-3 days, about 1-2 days, about 1 day, about 2 days, about 2.5 days, about 3 days, about 3.5 days, about 4 days). In some embodiments, the differentiation phase lasts for about 2, 3, 4, 5, 6, or 7 days.

Stem Cell Differentiation hEMP cells generated using the single cell, non-clustered approach according to the present disclosure can be further differentiated into various cell tell types.

Mesoderm Induction

The earliest CD326−CD56+ hEMP cells, generated from hESCs or iPSCs in the presence of activin A, BMP4, VEGF, and FGF2, represent a multipotent mesoderm-committed progenitor population. CD326−CD56+ progenitors are unique in their ability to generate all mesodermal lineages including hematopoietic, endothelial, mesenchymal (bone, cartilage, fat, fibroblast), smooth muscle, and cardiomyocytes, while lacking the pluripotency of hESCs or iPSCs. CD326−CD56+ hEMP cells are the precursors of more lineage-restricted mesodermal progenitors.

CD326−CD56+ hEMP cells may be produced with the combination of BMP4, VEGF, and bFGF and a transient exposure to activin A.

Selection of hEMP Cells

ESCs or iPSCs transitioning to hEMPs are characterized by the loss of CD326 EPCAM and gain of CD56 NCAM (CD326−CD56+). The epithelial marker CD326 is uniformly expressed at high levels in undifferentiated cells from human embryonic stem cell lines (e.g., H9, H1, and HESS) or iPSCs, whereas CD56 is not expressed in undifferentiated hESCs or iPSCs. After differentiation in mesoendoderm induction conditions, a population marked by loss of CD326 expression and acquisition of CD56 (CD326−CD56+) is clearly detectable.

Additionally, following hEMP differentiation, E-cadherin, CD326/TACSTD1, Claudin 3, Claudin 6, Claudin 7, Syndecan 1, Syndecan 2, Beta-catenin, Occludin, Nanog, Sox 2, and/or OCT4 may be downregulated. Following hEMP differentiation, Snail-1, Snail2/Slug, Twist 1, LEF1, ZEB1, MMP9, Fibronectin, Vimentin, and/or ZEB2 may be upregulated.

Regulation of hEMP cell markers may be determined by known techniques in the art including protein detection methods (e.g., flow cytometry, FACS, Western Blot, ELISA, HPLC, LC/MS, Protein Immunoprecipitation, immunoelectrophoresis, protein immunostaining, etc.) and nucleic acid detection methods (e.g., mRNA transcript analysis, Northern blotting, cDNA, DNA Microarray analysis, polymerase chain reaction, gene expression profiling, etc.).

Differentiation and Selection of T Cells hEMP cells have the potential to differentiate into hematoendothelial cells (e.g., blood, endothelium), cardiovascular (e.g., endothelium, cardiomyocytes, smooth muscle), and mesenchymal (e.g., smooth muscle, fibroblasts, bone, cartilage, fat). Lymphoid cells include T cells, B cells, and natural killer cells. T cells originate from hematopoietic stem cells in the bone marrow. Hematopoietic progenitors (e.g., hEMP cells) from hematopoietic stem cells populate the thymus and expand by cell division to generate a large population of immature thymocytes. The earliest thymocytes express neither CD4 nor CD8, however, as they progress through their development, they become double-positive (DP) thymocytes (CD4+CD8+), and eventually mature to single-positive (SP) (CD4+CD8− or CD4−CD8+) thymocytes that are then released from the thymus to peripheral tissues.

The increased efficiency and yield of hEMP cells according to the present disclosure leads to rapid and robust T lineage commitment. In some embodiments, T cells may be differentiated from hEMP cells in an ATO system. In some embodiments, T cells may be differentiated from hEMP cells using lentiviral transduction methods. In some embodiments, T cells may be differentiated from hEMP cells using stromal monolayers.

Differentiation of hEMP cells to T cells is indicated by the appearance of CD4+CD3-immature single positive (ISP) cells and CD4+CD8+(DP) cells. More mature CD3+ TCRαβ+ cells emerge, and increase over time. A smaller fraction of CD3+TCRγδ+ T cells may also be generated to progressively mature to CD8SP and, to a lesser extent, CD4SP T cells, consistent with positive selection in ATOs.

Flow cytometry analysis of thymic and ATO-derived T cell progenitors may be used to assess the following surface phenotypes: Early thymic progenitor (ETP; CD34+CD7−CD1a−), CD1a-pro-T (CD34+CD7+CD1a−), and CD1a+ pro-T (CD34+CD7+CD1a+); or CD5− pro-T (pro-T1; CD34+CD7+CD5−) and CD5+ pro-T (pro-T2; CD34+CD7+CD5+). Thymic and ATO-derived T cells and precursors are defined as CD14−CD56− in combination with the following phenotypes: total T lineage cells (CD7+CD5+), double negative (DN; CD4−CD8−), CD4 immature single positive (CD4 ISP; CD5+CD4+CD3−), double positive (DP; CD4+CD8+), CD8SP (CD3+TCRαβ+CD8+CD4−), CD4SP (CD3+TCRαβ+CD8−CD4+), immature naive (CD45RA−CD45RO+ that were CD8SP or CD4SP), mature naive (CD45RA+CD45RO− that were CD8SP or CD4SP). Immature and mature naive phenotypes are confirmed by co-staining for CD1a, CD27, CD28, and CCR7.

Artificial Thymic Organoid (ATO)

In vivo genetically modified murine models, humanized mice, and in vitro systems such as the OP9-DLL1 or recently described artificial thymic organoid (ATO) have shown multiple avenues by which stem cells may be modified or cultured to generate a desired mature T cell, including with antigen receptors against cancer antigens.

Pluripotent stem cells and/or hEMPs according to the present disclosure may be further differentiated in the OP9-DLL1 or Artificial Thymic Organoid (ATO) cell culture system. An ATO is a serum-free, 3-dimensional cell culture technology that recapitulates T-cell differentiation. ATO technology has the potential to generate off-the-shelf engineered T cells to treat cancer and other diseases.

A suitable artificial thymic organoid (ATO) system supports highly efficient in vitro differentiation and positive selection of native and TCR-engineered human T cells from cord blood, bone marrow, and peripheral blood HSPCs. ATO-derived T cells exhibit a naïve phenotype, diverse TCR repertoire, and TCR-dependent activation and proliferation. ATO-derived engineered T cells also mature to a naïve phenotype and furthermore show antigen specific tumor killing in vitro and in vivo. ATOs thus present an efficient method for the generation of mature naïve and potentially non-alloreactive engineered T cells for adoptive cell therapy. Exemplary methods for producing engineered T cells with the ATO culture system are described in, for example, Seet C S, He C, Bethune M T, et al. Generation of mature T cells from human hematopoietic stem/progenitor cells in artificial thymic organoids. Nature methods. 2017; 14(5):521-530. doi:10.1038/nmeth.4237, the contents of which is incorporated herein by reference.

Highly pure populations of T cells are readily collected from ATOs by mechanical dissociation and can be further purified by standard methods to remove the <0.5% of contaminating stromal cells. ATO cell yield per stem cell, or progenitor cell is inversely related to the number of cells (e.g., hEMP cells) seeded and the ratio of input cells to stromal cells.

The ATO system is able to support the differentiation and positive selection of human T cells from progenitor cells (e.g., hEMP cells) while retaining key translational properties such as standardized components, reproducibility, and scalability suitable for the generation of T cells for therapeutic applications. The present disclosure provides the means for remarkable fidelity of T cell differentiation in ATOs compared to the human thymus, culminating in the emergence of bona fide naïve T cells similar to those found in the thymus and blood.

ATOs supplied with progenitor cells according to the present disclosure support robust in vitro differentiation, positive selection, and maturation of human T cells. ATO-derived mature T cells exhibit an antigen naive phenotype, diverse TCR repertoire, and activation/proliferation in response to antigenic stimuli. ATOs also support highly efficient differentiation of TCR-engineered antigen-specific T cells from progenitor cells specific for tumor-associated antigens.

Cells

The cell of the present disclosure may be obtained through any source known in the art. For example, T cells can be differentiated in vitro from a hematopoietic stem cell population or pluripotent stem cells, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In certain embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semi-automated flow-through centrifuge, e.g., the Cobe™ 2991 cell processor, the Baxter CytoMate™, or the like. In some embodiments, the washed cells are resuspended in one or more biocompatible buffers, or other saline solution with or without buffer. In certain embodiments, the undesired components of the apheresis sample are removed. Additional methods of isolating T cells for a T cell therapy are disclosed in U.S. Patent Publication No. 2013/0287748, which is herein incorporated by references in its entirety.

In certain embodiments, stem cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for CD4+ cells by negative selection, a monoclonal antibody cocktail typically includes antibodies to CD8, CD11b, CD14, CD16, CD20, and HLA-DR. In certain embodiments, flow cytometry and cell sorting are used to isolate cell populations of interest for use in the present disclosure.

In some embodiments, CD8+ cells are further sorted into naive, stem cell memory, central memory, effector memory, and effector cells by identifying cell surface antigens that are associated with each of these types of CD8+ cells. In some embodiments, the expression of phenotypic markers of central memory T cells includes CCR7, CD3, CD28, CD45RO, CD62L, and CD127 and are negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In certain embodiments, CD4+ T cells are further sorted into subpopulations. For example, CD4+T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, pluripotent stem cells are modified before being induced to hEMPs. In another embodiment, transduced hEMPs are processed through the ATO. In another embodiment, the immune cells, e.g., T cells, are genetically modified with a chimeric antigen receptor or TCR (e.g., transduced with a viral vector comprising one or more nucleotide sequences encoding a CAR or TCR) and then are activated and/or expanded in vitro. Methods for activating and expanding T cells are known in the art and are described, e.g., in U.S. Pat. Nos. 6,905,874, 6,867,041, and 6,797,514, and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177, 5,827,642, and PCT Publication No. WO 2012/129514, the contents of which are hereby incorporated by reference in their entirety.

In certain embodiments, the T cells are obtained from a donor subject. In some embodiments, the donor subject is human patient afflicted with a cancer or a tumor. In other embodiments, the donor subject is a human patient not afflicted with a cancer or a tumor.

Other aspects of the present disclosure are directed to compositions comprising a polynucleotide described herein, a vector described herein, a polypeptide described herein, or an in vitro cell described herein. In some embodiments, the composition comprises a pharmaceutically acceptable carrier, diluent, solubilizer, emulsifier, preservative, and/or adjuvant. In some embodiments, the composition comprises an excipient.

In other embodiments, the composition is selected for parenteral delivery, for inhalation, or for delivery through the digestive tract, such as orally. The preparation of such pharmaceutically acceptable compositions is within the ability of one skilled in the art. In certain embodiments, buffers are used to maintain the composition at physiological pH or at a slightly lower pH, typically within a pH range of from about 5 to about 8. In certain embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In certain embodiments, the vehicle for parenteral injection is sterile distilled water in which composition described herein, with or without at least one additional therapeutic agent, is formulated as a sterile, isotonic solution, properly preserved. In certain embodiments, the preparation involves the formulation of the desired molecule with polymeric compounds (such as polylactic acid or polyglycolic acid), beads or liposomes, that provide for the controlled or sustained release of the product, which are then be delivered via a depot injection. In certain embodiments, implantable drug delivery devices are used to introduce the desired molecule or cells.

Cancer Treatment

The methods of the disclosure can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In certain embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammopathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T-cell acute lymphoid leukemia ("TALL"), T-cell lymphoma, transformed follicular lymphoma, Waldenstrom macroglobulinemia, or a combination thereof.

In one embodiment, the cancer is a myeloma. In one particular embodiment, the cancer is multiple myeloma. In another embodiment, the cancer is a leukemia. In one embodiment, the cancer is acute myeloid leukemia.

In some embodiments, the methods further comprise administering a chemotherapeutic. In certain embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750, which are incorporated by reference in their entirety herein. These describe, e.g., methods of conditioning a patient in need of a T cell therapy comprising administering to the patient specified beneficial doses of cyclophosphamide (between 200 mg/m2/day and 2000 mg/m2/day) and specified doses of fludarabine (between 20 mg/m2/day and 900 mg/m2/day). One such dose regimen involves treating a patient comprising administering daily to the patient about 500 mg/m2/day of cyclophosphamide and about 60 mg/m2/day of fludarabine for three days prior to administration of a therapeutically effective amount of engineered T cells to the patient.

In other embodiments, the antigen binding molecule, transduced (or otherwise engineered) cells (such as CARs or TCRs), and the chemotherapeutic agent are administered each in an amount effective to treat the disease or condition in the subject.

In certain embodiments, compositions comprising CAR- and/or TCR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks, from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche).

Additional therapeutic agents suitable for use in combination with the disclosure include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept,adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR- and/or TCR-containing immune are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, and triamcinolone), nonsteroidal anti-inflammatory drugs (NSAIDS) including aspirin, ibuprofen, naproxen, methotrexate, sulfasalazine, leflunomide, anti-TNF medications, cyclophosphamide, and mycophenolate. Exemplary NSAIDs include ibuprofen, naproxen, naproxen sodium, Cox-2 inhibitors, and sialylates. Exemplary analgesics include acetaminophen, oxycodone, and tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In certain embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

Another aspect of the present disclosure is directed to a method of inducing an immunity against a tumor comprising administering to a subject an effective amount of a modified T cell disclosed herein. Another aspect of the present disclosure is directed to a method of inducing an immune response in a subject comprising administering an effective amount of the engineered immune cells of the present application. In some embodiments, the immune response is a T cell-mediated immune response. In some embodiments, the T cell-mediated immune response is directed against one or more target cells. In some embodiments, the engineered immune cell comprises a CAR or a TCR, wherein the CAR or the TCR comprises a THD described in the present disclosure. In some embodiments, the target cell is a tumor cell.

Another aspect of the present disclosure is directed to a method for treating or preventing a malignancy, said method comprising administering to a subject in need thereof an effective amount of at least one immune cell, wherein the immune cell comprises at least one CAR or TCR.

Another aspect of the present disclosure is directed to a method of treating a cancer in a subject in need thereof comprising administering to the subject a polynucleotide, a vector, a CAR or a TCR, a cell, or a composition disclosed herein. In one embodiment, the method comprises administering a polynucleotide encoding a CAR or a TCR. In another embodiment, the method comprises administering a vector comprising a polynucleotide encoding a CAR or a TCR. In another embodiment, the method comprises administering a CAR or a TCR encoded by a polynucleotide disclosed herein. In another embodiment, the method comprises administering a cell comprising the polynucleotide, or a vector comprising the polynucleotide, encoding a CAR or a TCR.

In some embodiments, the donor T cells for use in the T cell therapy are obtained from the patient (e.g., for an autologous T cell therapy). In other embodiments, the donor stem cells to be differentiated into T cells for use in the T cell therapy are obtained from a subject that is not the patient.

The T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In one particular embodiment, the therapeutically effective amount of the CAR T cells or the TCR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

Immune Tolerance

The methods of the disclosure can be used to treat an immune tolerance disease in a subject. In certain embodiments, the methods induce a complete response. In other embodiments, the methods induce a partial response.

Deficits in central or peripheral tolerance can cause autoimmune disease, resulting in syndromes such as systemic lupus erythematosus, rheumatoid arthritis, type 1 diabetes, autoimmune polyendocrine syndrome type 1 (APS-1), and immunodysregulation polyendocrinopathy enteropathy X-linked syndrome (IPEX), and potentially contribute to asthma, allergy, and inflammatory bowel disease. Immune tolerance can also be problematic in transplantation rejection for example stem cell transplant, kidney transplant, liver transplant, etc.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present disclosure. To the extent that any of the definitions or terms provided in the references incorporated by reference differ from the terms and discussion provided herein, the present terms and definitions control.

The present disclosure is further illustrated by the following examples, which should not be construed as further limiting. The contents of all references cited throughout this application are expressly incorporated herein by reference.

EXAMPLES

Example 1: Comparison of hEMP Induction Between Clusters and Single Cells

This example illustrates a comparison of hEMP induction between clusters and single cells.

A confluent plate of ES cells as clusters were manually passaged and plated at 20%, 40%, and 80% equivalent of the well into Matrigel® coated 6-well plates. Additionally, a confluent plate of ES cells was chemically disrupted by enzymatic digestion and counted to determine the number of cells/surface area. Single cells were seeded at $1.8 \times 10^6$ (20% confluent), $3.6 \times 10^6$ (40% confluent), and $7.2 \times 10^6$ (80% confluent). Cells were cultured in either mTeSR1 medium known to maintain ES cells in an undifferentiated state as a control, or in X-VIVO™-15 hEMP push medium. In all conditions, the small molecule Y27632 ROCK inhibitor was included to aid in the survival of ES cells during passage. Cells were harvested at all conditions on d1, d2, d3, and d4. A map of the experiment is shown in tables 1, 2, and 3.

TABLE 1

| Density | Cell form | Medium | Harvest(d) |
|---|---|---|---|
| $1.8 \times 10^6$ cells/well (~20%) | Clusters | mTeSR1 | 1 |
| | | | 2 |
| | | | 3 |
| | | | 4 |
| | | X-VIVO ™15 | 1 |
| | | | 2 |
| | | | 3 |
| | | | 4 |
| | Single Cells | mTeSR1 | 1 |
| | | | 2 |
| | | | 3 |
| | | | 4 |
| | | X-VIVO ™15 | 1 |
| | | | 2 |
| | | | 3 |
| | | | 4 |

TABLE 3

| Density | Cell form | Medium | Harvest(d) |
|---|---|---|---|
| $7.2 \times 10^6$ cells/well (~80%) | Clusters | mTeSR1 | 1 |
| | | | 2 |
| | | | 3 |
| | | | 4 |
| | | X-VIVO ™15 | 1 |
| | | | 2 |
| | | | 3 |
| | | | 4 |
| | Single Cells | mTeSR1 | 1 |
| | | | 2 |
| | | | 3 |
| | | | 4 |
| | | X-VIVO ™15 | 1 |
| | | | 2 |
| | | | 3 |
| | | | 4 |

TABLE 2

| Density | Cell form | Medium | Harvest(d) |
|---|---|---|---|
| $3.6 \times 10^6$ cells/well (~40%) | Clusters | mTeSR1 | 1 |
| | | | 2 |
| | | | 3 |
| | | | 4 |
| | | X-VIVO ™15 | 1 |
| | | | 2 |
| | | | 3 |
| | | | 4 |
| | Single Cells | mTeSR1 | 1 |
| | | | 2 |
| | | | 3 |
| | | | 4 |
| | | X-VIVO ™15 | 1 |
| | | | 2 |
| | | | 3 |
| | | | 4 |

Figure 2:
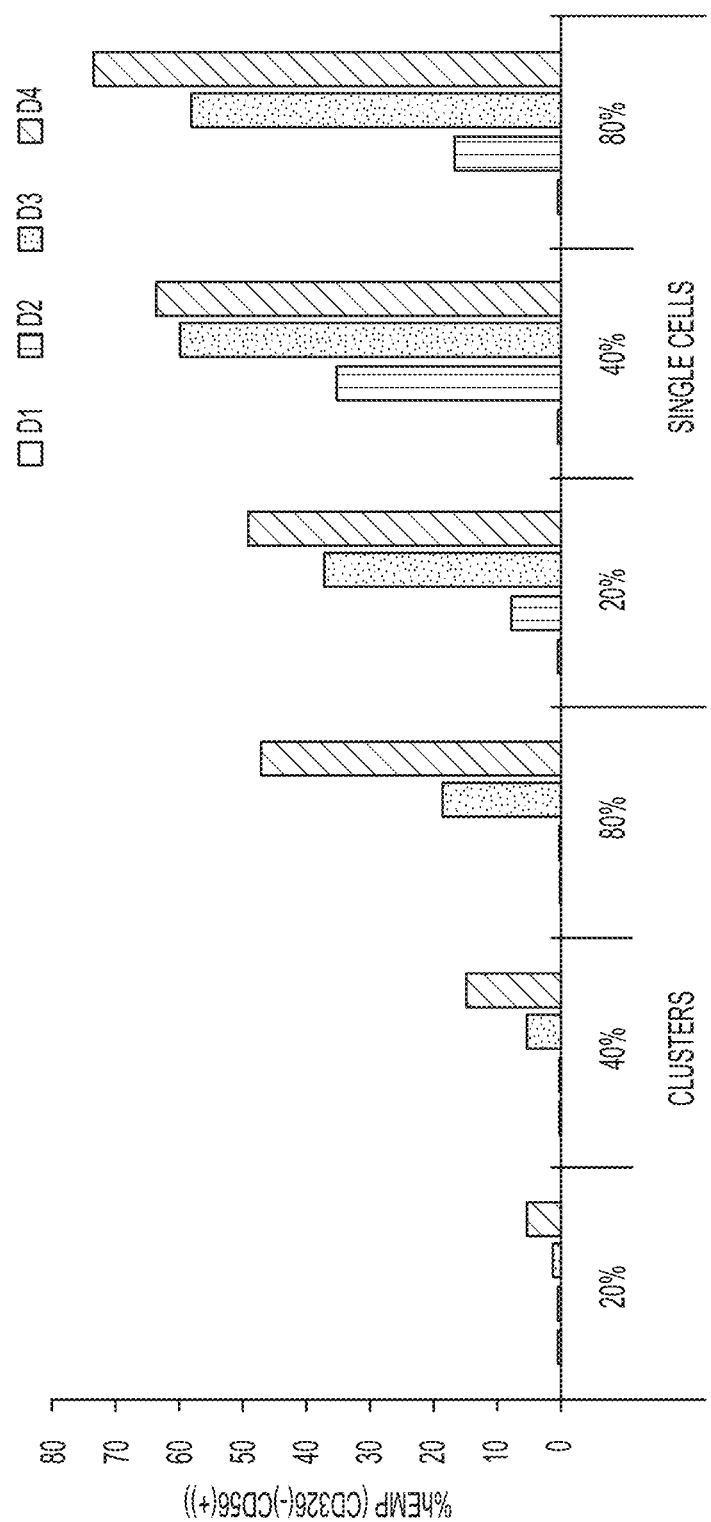
FIG. 2 shows a summary graph of the exemplary flow cytometry data illustrating the change in surface expressed CD326 and CD56.
Figure 3:
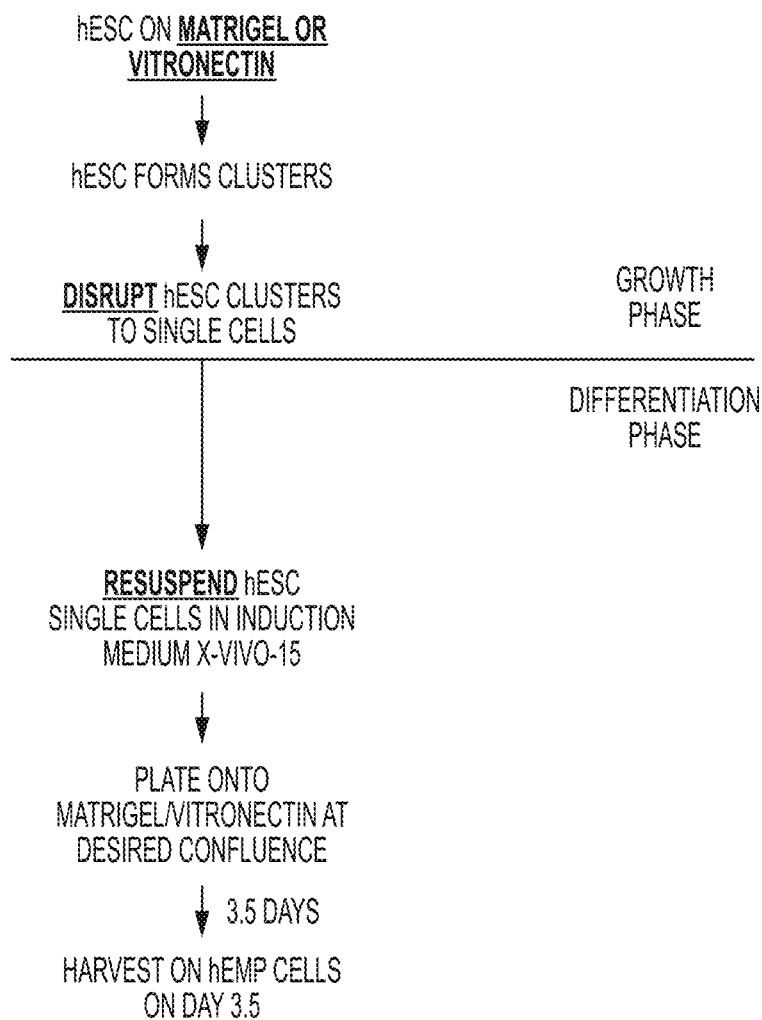
FIG. 3 shows an exemplary flow chart for the generation of hEMP cells from ES or iPS cells.

ES cells transitioning to hEMPs are characterized by the loss of CD326 EPCAM and gain of CD56 NCAM. Phenotypic analysis based on the change in surface expressed CD326 and CD56 indicate that a single cell approach is more efficient than a cluster based approach at generating hEMPs with an optimal density between $1.8-7.2 \times 10^6$ cells/well in a 6-well plate, or $2.53-7.58 \times 10^5$ cells/cm$^2$. Exemplary flow cytometry data and a summary graph illustrating the change in surface expressed CD326 and CD56 are shown in FIG. 1 and FIG. 2, respectively. An exemplary process for the generation of hEMP cells is shown in FIG. 3.

Example 2: Comparison of Matrigel® and Vitronectin in Mesoderm Push, and Evaluation of Cell Expansion This example provides a comparison of hEMP induction in the presence of Matrigel® or vitronectin. To investigate the effect of removal of Matrigel®, an undefined product produced by murine sarcoma cells, from the hEMP induction process, mesoderm push experiments were performed.

Single cells were seeded at 5% or 40% confluence in 6-well plates coated with either Matrigel® (tissue culture treated plate) or recombinant human vitronectin (non-tissue culture treated plate). Cells were grown for 3 days, and a portion of cells were passaged and replated at 5% or 40% density onto fresh coated plates, and grown for another 3 days. Cells were harvested and assessed for CD326 and CD56 expression. A summary of the experimental design is shown in Table 4.

TABLE 4

| Seeding (d0) | Passage (d3) | Harvest(d6) |
|---|---|---|
| 5% | No | Yes |
| | to 5% | Yes |
| | ~~to 40%~~ | N/A |
| 40% | No | Yes |
| | to 5% | Yes |
| | to 40% | Yes |

Figure 4:
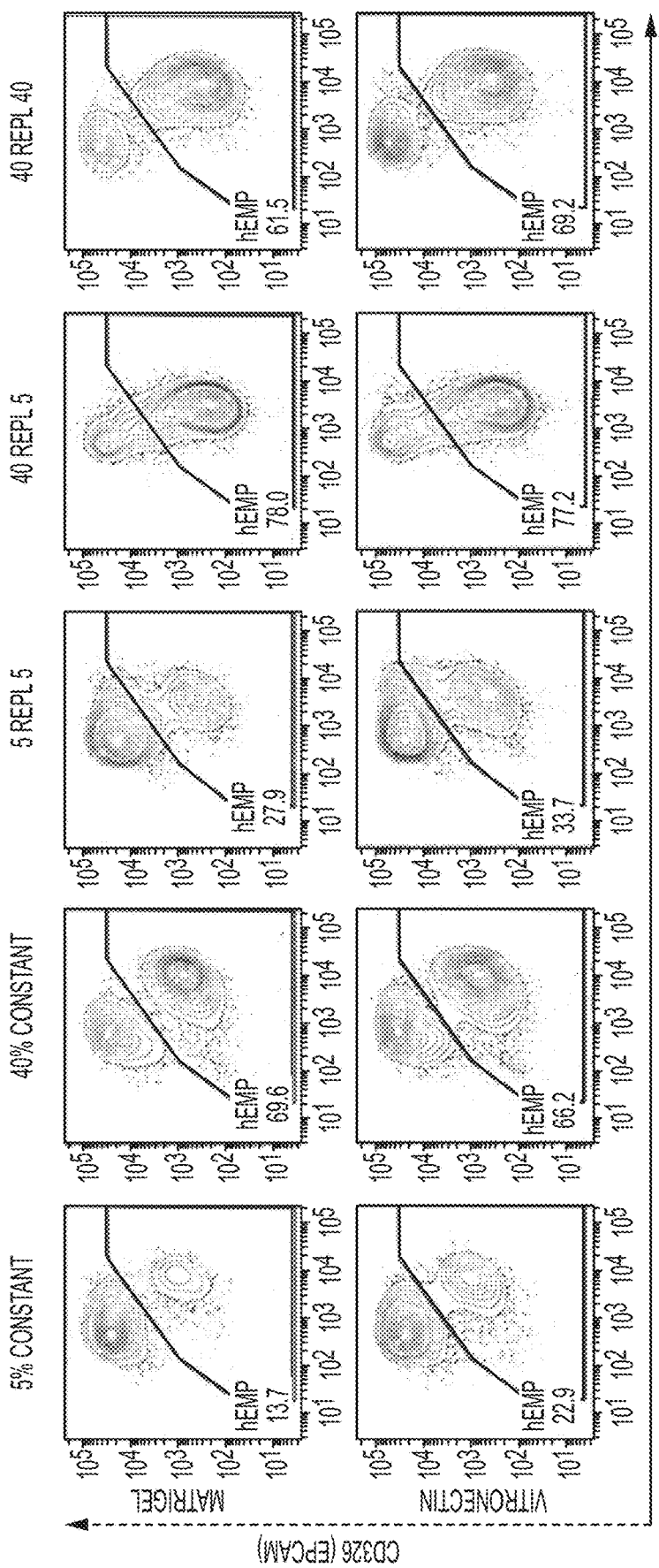
FIG. 4 shows exemplary flow cytometry data illustrating the change in surface expressed CD326 and CD56 on Matrigel® and vitronectin substrates.
Figure 5:
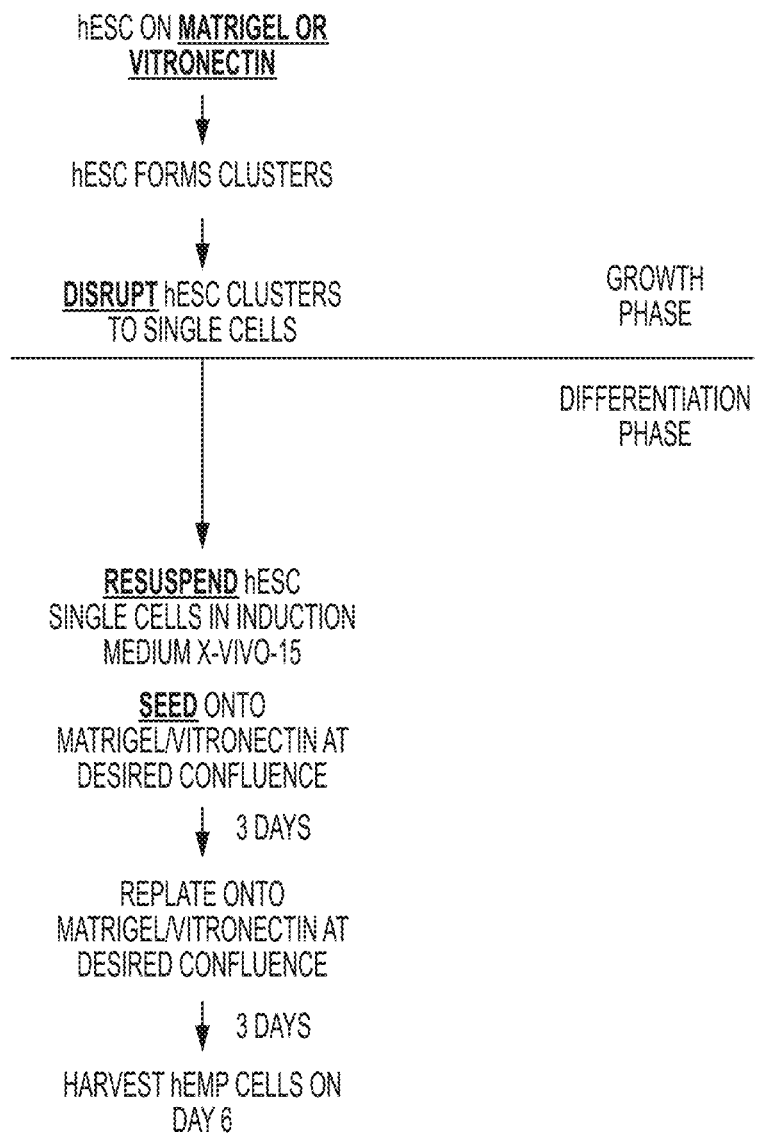
FIG. 5 shows an exemplary flow chart for the generation of hEMP cells from ES or iPS cells.

As shown in FIG. 4, an equivalent hEMP phenotype between Matrigel® and vitronectin coated surfaces was observed in all experimental conditions tested. Recombinant human vitronectin is at least equivalent to Matrigel® as a substrate on which to differentiate hEMPs from ES cells. Interestingly, as summarized in Table 5 and Table 6, an initial seeding density of 40% split to 5% density at d3 allowed for expansion of hEMPs approximately 10-fold (13.31) from the number of input ES cells. An exemplary process for the generation of hEMP cells including a seeding step is shown in FIG. 5.

TABLE 6

| Vitronectin | Fold Expansion | hEMP/ES |
|---|---|---|
| 5% Constant | 7.67 | 1.76 |
| 40% Constant | 3.64 | 2.41 |
| 5% to 5% | 13.35 | 5.16 |
| 40% to 5% | 17.24 | 13.31 |
| 40% to 40% | 10.08 | 6.98 |

TABLE 5

| Matrigel | Fold Expansion | hEMP/ES |
|---|---|---|
| 5% Constant | 7.67 | 1.05 |
| 40% Constant | 3.63 | 2.52 |
| 5% to 5% | 15.41 | 4.30 |
| 40% to 5% | 16.63 | 12.97 |
| 40% to 40% | 12.24 | 9.97 |

Figure 6:
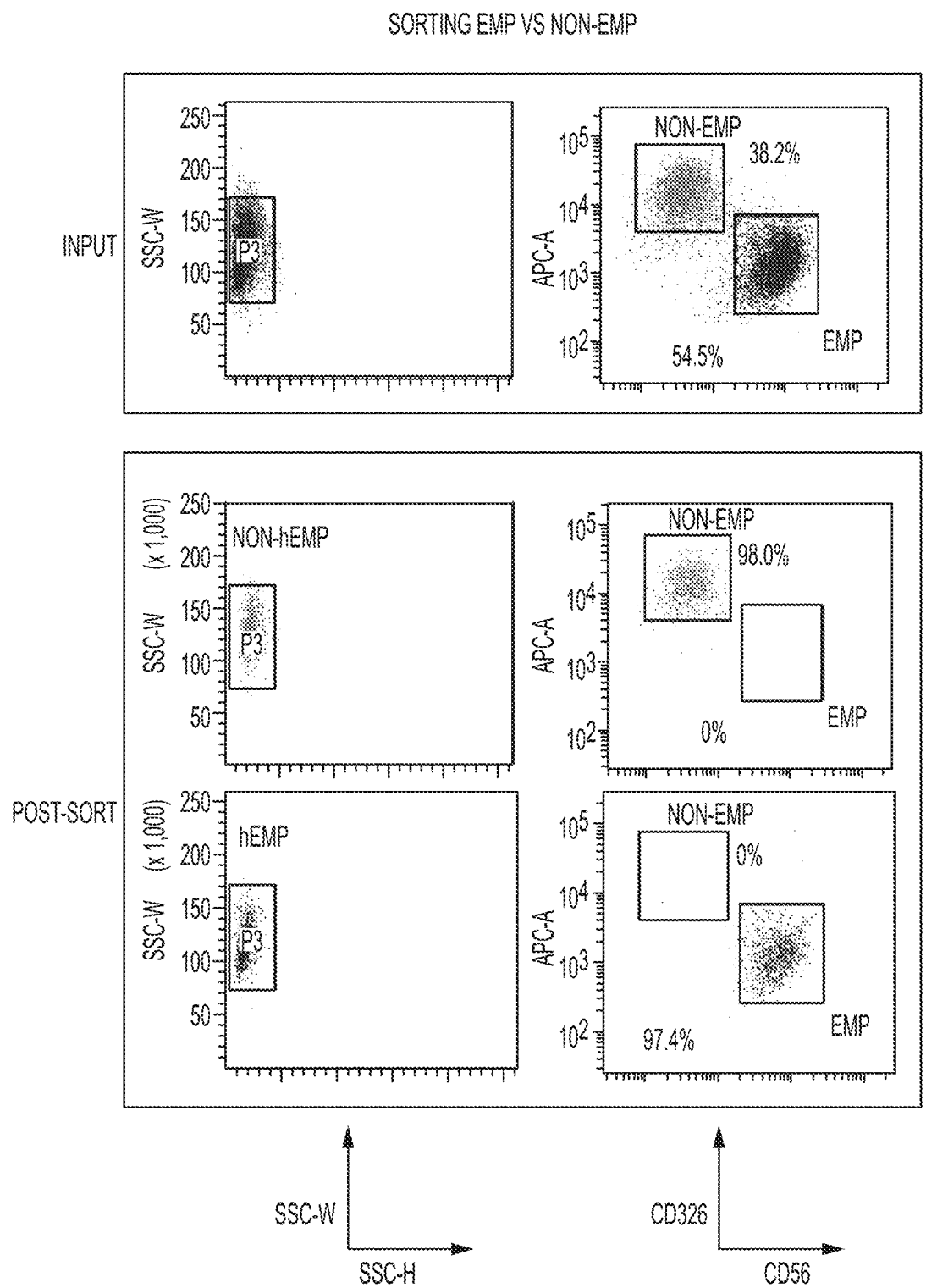
FIG. 6 shows flow cytometry data illustrating cells were purity of induced and sorted hEMP cells. Post-sort purity was determined at >95% for both non-hEMP and hEMP cells.

Example 3: Differentiation of hEMP Cells into T Cells hEMP cells generated according to the non-clustered cell approach of the present disclosure can be used to increase efficiency of T cell differentiation in in vitro systems (e.g., ATO system). hEMP cells were induced as described, and sorted on a FACSAria Fusion (BD). Post-sort purity was determined at >95% for both non-hEMP and hEMP (FIG. 6). T cell differentiation was induced using serum free ATO culture medium ("RB27") composed of RPMI 1640 (Corning, Manassas, Va.), 2% XenoFree B27 (ThermoFisher Scientific, Grand Island, N.Y.), 30 µM L-ascorbic acid 2-phosphate sesquimagnesium salt hydrate (Sigma-Aldrich, St. Louis, Mo.) reconstituted in PBS, 1% penicillin/streptomycin (Gemini Bio-Products, West Sacramento, Calif.), 1% Glutamax (ThermoFisher Scientific, Grand Island, N.Y.), 5 ng/ml rhFLT3L, 5 ng/ml rhIL-7, and 50 ng/ml SCF (Peprotech, Rocky Hill, N.J.). 2% XenoFree B27 was substituted for B27.

$0.5 \times 10^6$ MS5-hDL4 cells were combined with $1 \times 10^4$ purified hEMP cells per ATO in 50 ml conical vials and centrifuged at 500 g for 5 min. in a swinging bucket centrifuge. Supernatants were carefully removed and the cell pellet was resuspended by brief vortexing. For each ATO, a 0.4 µm Millicell transwell insert (EMD Millipore, Billerica, MA; Cat. PICMORG50) was placed in a 6-well plate containing 1 ml RB27 per well. To plate ATOs, inserts were taken out and rested on the edge of plate to drain excess medium. The cell slurry was adjusted to 5 µl per ATO, drawn up in with a 20 µl pipet tip, and plated by forming a drop at the end of the pipet tip, which was gently deposited onto the cell insert. The cell insert was placed back in the well containing 1 mL RB27. Medium was changed completely every 3-4 days by aspiration from around the cell insert followed by replacement with 1 ml with fresh RB27/cytokines. ATOs were cultured in this fashion for up to 8 weeks. ATO cells were harvested by adding FACS buffer (PBS/0.5% bovine serum album/2 mM EDTA) to each well and briefly disaggregating the ATO by pipetting, followed by passage through a 70 µm nylon strainer.

Figure 7:
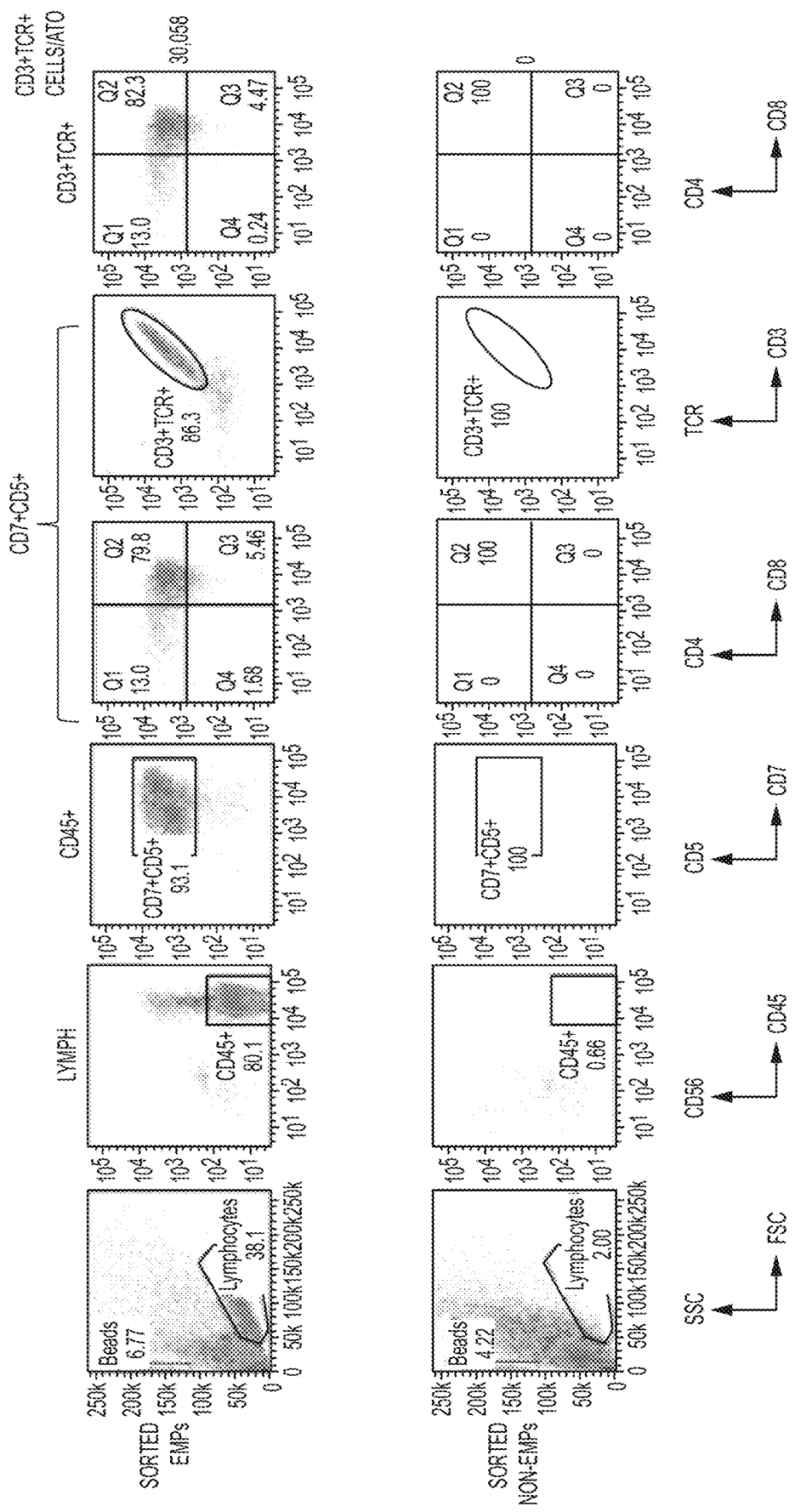
FIG. 7 shows flow cytometry data illustrating analysis of T cell development at week 4. Harvested cells were stained with antibodies for the following antigens: CD45, CD56, CD3, CD4, CD8, TCRab.

Harvested cells were stained with antibodies for the following antigens: CD45, CD56, CD3, CD4, CD8, TCRab (Biolegend) for 30' at 4 C in the dark. Cells were washed with PBS and analyzed on a Fortessa X20 (BD) for analysis of T-cell development. An example of cells at week 4 is shown in FIG. 7.

We claim:

1. A method of generating human embryonic mesenchymal progenitor (hEMP) cells, the method comprising the steps of:
   (a) incubating clusters of human pluripotent stem cells with a Trypsin-like enzyme to generate nonclustered single stem cells;
   (b) transferring the non-clustered single stem cells to a serum-free induction medium to induce differentiation of the stem cells into human embryonic mesenchymal progenitor (hEMP) cells;
   (c) seeding the non-clustered single stem cells on a substrate coated with recombinant human vitronectin, but not mouse embryonic fibroblasts (MEFs), at a defined single cell density of $7.2 \times 10^5$ cells/cm$^2$ or $7.58 \times 105$/cm$^2$ to induce differentiation of the stem cells into hEMP cells; and
   (d) cultivating the cells under culture conditions that facilitate cell growth to a desired confluence, wherein the culture conditions comprise a ROCK inhibitor, Y27632;
   thereby generating hEMP cells.

2. The method of claim 1, wherein the stem cells are human embryonic stem (ES) cells or induced pluripotent stem (iPS) cells.

3. The method of claim 1, wherein the substrate is a welled plate, a cell culture dish, a membrane, a bag, a culture flask, an inverse opal, a polymer lattice, a static cell suspension, an agitated cell suspension, or a plasma treated polymer.

4. The method of claim 1, wherein the desired confluence is between about 20% and about 80%.

5. The method of claim 1, wherein incubation time is between about 2 and about 4 days.

6. The method of claim 1, further comprising the step of differentiating the hEMP cells into T cells.

7. The method of claim 1, wherein the Trypsin-like enzyme is Trypsin, collagenase, or Trypsin-EDTA.

8. The method of claim 2, wherein the ES or iPS cells are H1 cells, H9 cells, HES3 cells, HSF1 cells, HSF6 cells, ESI-017 cells, CS02iCTR-NTn1 cells, CS03iCTR-NTn1 cells, CS80iCTR-Tn3 cells, CS179iCTR-NTn1 cells, CS201iCTR-NTn4 cells, CS202iCTR-NTn2 cells, or CS206iCTR-Tn5 cells.

9. The method of claim 3, wherein the substrate comprises a membrane.

10. The method of claim 4, wherein the confluence is about 20%, about 30%, about 40%, about 50%, about 60%, about 70% or about 80%.

11. The method of claim 5, wherein the incubation time is about 2.0, about 2.5, about 3.0, about 3.5 or about 4.0 days.

12. The method of claim 11, wherein the incubation time is about 3.5 days.

13. The method of claim 1, wherein the stem cells are seeded on the substrate at a confluence of about 40%.

14. The method of claim 1, wherein the stem cells are seeded on the substrate at a confluence of about 40% and then split to a confluence of about 5%.

15. The method of claim 1, wherein the stem cells are seeded on the substrate at a confluence of about 40% and then split to a confluence of about 5% after about 3.0 days.

16. The method of claim 1, wherein the serum-free induction medium comprises BMP4, VEGF, FGF, and a transient exposure to activin A.

* * * * *